United States Patent [19]

Rivier et al.

[11] 4,409,208

[45] * Oct. 11, 1983

[54] GNRH ANTAGONISTS

[75] Inventors: Jean E. F. Rivier; Wylie W. Vale, Jr., both of La Jolla, Calif.

[73] Assignee: The Salk Institute for Biological Studies, San Diego, Calif.

[ * ] Notice: The portion of the term of this patent subsequent to Sep. 29, 1998 has been disclaimed.

[21] Appl. No.: 256,063

[22] Filed: Apr. 21, 1981

Related U.S. Application Data

[63] Continuation-in-part of Ser. No. 140,487, Apr. 15, 1980, Pat. No. 4,292,313, and Ser. No. 182,594, Aug. 29, 1980, abandoned.

[51] Int. Cl.$^3$ .................... A61K 37/00; C07C 103/52
[52] U.S. Cl. .......................... 424/177; 260/112.5 LH
[58] Field of Search ............... 260/112.5 LH; 424/177

[56] References Cited

U.S. PATENT DOCUMENTS 3,933,782  1/1976  Yardley et al. ............. 260/112 LH
4,234,571 11/1980  Nestor et al. ............. 260/112.5 LH
4,253,997  3/1981  Sarantakis ................. 260/112.5 LH

OTHER PUBLICATIONS

Journal of Medicinal Chemistry, 18, (1975), 1247–1250.
Biochem. and Biophys. Res. Comm., vol. 66, No. 1, (1975), pp. 336–343, Prasad et al., "Synthesis and Biological Activity of Antagonists of Luteinizing Hormone-Releasing Hormone, (LH–RH).
Chemical Pharm. Bull., vol. 24, No. 12, pp. 3149–3157, (1976) Yabe et al., "Analogues of Luteinizing Hormone-Releasing Hormone with Modification in Position 3$^1$".

*Primary Examiner*—Delbert R. Phillips
*Attorney, Agent, or Firm*—Fitch, Even, Tabin & Flannery

[57] ABSTRACT

Peptides which inhibit the secretion of gonadotropins by the pituitary gland and inhibit the release of steroids by the gonads. Administration of an effective amount prevents ovulation of female mammalian eggs and/or the release of steroids by the gonads. The peptides have the structure.

$$X\text{-}R_1\text{-}R_2\text{-}R_3\text{-}Ser\text{-}Tyr\text{-}R_4\text{-}R_5\text{-}Arg\text{-}Pro\text{-}R_6$$

wherein X is hydrogen or an acyl group having 7 or less carbon atoms; $R_1$ is dehydro Pro or dehydro D-Pro; $R_2$ is D-Phe, Cl-D-Phe, dichloro-D-Phe, $CF_3$-D-Phe, F-D-Phe, difluoro-D-Phe, AcNH-D-Phe, $NO_2$-D-Phe, dinitro-D-Phe, Br-D-Phe, dibromo-D-Phe, $CH_3$-S-D-Phe, $OCH_3$-D-Phe or $CH_3$-D-Phe; $R_3$ is D-Trp or $\beta$-(naphthyl)-D-Ala; $R_4$ is a D-isomer aromatic amino acid or $\beta$-(naphthyl)-D-Ala; $R_5$ is Leu or N$\alpha$Me-Leu; and $R_6$ is Gly-$NH_2$ or $NHCH_2CH_3$; provided however that either $R_3$ or $R_4$ is $\beta$-(naphthyl)-D-Ala.

16 Claims, No Drawings

GNRH ANTAGONISTS

The invention described herein was made in the course of work under a grant or award from the Department of Health and Human Services.

This application is a continuation-in-part of our earlier applications Ser. No. 140,487, filed Apr. 15, 1980, now U.S. Pat. No. 4,292,313 and Ser. No. 182,594 filed Aug. 29, 1980 now abandoned.

The present invention relates to peptides which inhibit the release of gonadotropins by the pituitary gland in mammalians, including humans and to methods of preventing ovulation and/or inhibiting the release of steroids. More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH. The hypothalamic hormone which acts as a releasing factor for LH is referred to herein as GnRH although it has also been referred to as LH-RH and as LRF. GnRH has been isolated and chaaracterized as a decapeptide having the following structure:

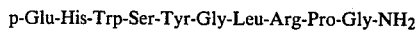

p-Glu-His-Trp-Ser-Tyr-Gly-Leu-Arg-Pro-Gly-NH$_2$

Peptides are compounds which contain two or more amino acids in which the carboxyl group of one acid is linked to the amino group of the other acid. The formula for GnRH, as represented above, is in accordance with conventional representation of peptides where the amino group appears to the left and the carboxyl group to the right. The position of the amino acid residue is identified by numbering the amino acid residues from left to right. In the case of GnRH, the hydroxyl portion of the carboxyl group of glycine has been replaced with an amino group (NH$_2$). The abbreviations for the individual amino acid residues above are conventional and are based on the trivial name of the amino acid, e.g. p-Glu is pyroglutamic acid, His is histidine, Trp is tryptophan, Ser is serine, Tyr is tyrosine, Gly is glycine, Leu is Leucine, Arg is arginine, Pro is proline, Phe is phenylalanine and Ala is alanine. Except for glycine, amino acids of the peptides of the invention are of the L-configuration unless noted otherwise.

It is well known that the substitution of D-amino acids for Gly in the 6-position of the GnRH decapeptide provides a peptide material having from about 1 to 35 times greater potency than does GnRH to effect the release of LH and other gonadotropins by the pituitary gland of mammalians. It is taught by K. U. Prasad et al. J. Med. Chem., Vol. 19, 492 (1976) that greater potency is also achieved by the substitution in the 3-position of 3-(1-naphthyl) Ala. The releasing effect is obtained when the GnRH analog is administered to a mammalian intravenously, subcutaneously, intramuscularly, orally, intranasally or intravaginally.

It is also known that substitution of various amino acids for His (or the deletion of His) at the 2-position of the GnRH decapeptide produces analogs having an inhibitory effect on the release of LH and other gonadotropins by the pituitary gland of mammalians.

Some female mammalians who have no ovulatory cycle and who show no pituitary or ovarian defect begin to secrete normal amounts of the gonadotropins LH and FSH after the appropriate administration of GnRH. Thus, the administration of GnRH is considered suitable for the treatment of those cases of infertility where a functional defect resides in the hypothalamus.

There are also reasons for desiring to prevent ovulation in female mammalians, and the administration of GnRH analogs that are antagonistic to the normal function of GnRH have been used to prevent ovulation. For this reason, analogs of GnRH which are antagonistic to GnRH are being investigated for their potential use as a contraceptive or for regulating conception periods. It is desired to provide peptides which are strongly antagonistic to endogenous GnRH and which prevent secretion of LH and the release of steroids by the gonads of mammals.

SUMMARY OF THE INVENTION

The present invention provides peptides which inhibit the release of gonadotropins in mammalians, including humans, and also provides methods for inhibiting the release of steroids by the gonads of male and female mammalians. The improved GnRH analogs are antagonistic to GnRH and have an inhibitory effect on the reproduction processes of mammalians. These analogs may be used to inhibit the production of gonadotropins and sex hormones under various circumstances including precocious puberty, hormone dependent neoplasia, dysmenorrhea and endometriosis.

Generally, in accordance with the present invention, peptides have been synthesized which strongly inhibit the secretion of gonadotropins by the pituitary gland of mammalians, including humans, and/or inhibit the release of steroids by the gonads. These peptides are analogs of GnRH wherein there is a 1-position substitution in the form of dehydroproline, a 3- and/or 6-position substitution in the form of β-(naphthyl) D-alanine and preferably a substituent is also present in the 2-position. The 1-position substituent may be modified so that its alpha amino group contains an acyl group, such as formyl, acetyl, acrylyl, vinylacetyl or benzoyl. Dehydro L-Pro is preferred in the 1-position. Modified D-Phe is preferably present in the 2-position and provides increased antagonistic activity as a result of the specific modifications present in the benzene ring. Single substitutions for hydrogen are preferably made in the para- or 4-position, and double substitutions are made preferably in the 2,4- or the 3,4-positions. The substitutions are most preferably selected from chloro, dichloro, methyl, fluoro, difluoro, trifluoromethyl, methoxy, bromo, dibromo, nitro, dinitro, acetylamino and methyl mercapto. β-(naphthyl) D-Ala is preferred in the 3-position; however, D-Trp may be used. β-(naphthyl) D-Ala or imBzl D-His or D-Trp or some other lipophilic aromatic D-amino acid is preferred in the 6-position, although any D-isomer amino acid, e.g., D-Leu and D-Ser(O-t But), may be used. The substitutions in the 7- and 10-positions are optional.

Because these peptides are highly potent to inhibit release of LH, they are often referred to as GnRH antagonists. The peptides inhibit ovulation of female mammals when administered at very low levels at proestrous and are also effective to cause resorption of fertilized eggs if administered shortly after conception. These peptides are also effective for the contraceptive treatment of male mammals.

DETAILED DESCRIPTION OF THE PREFERRED EMBODIMENTS

More specifically, the peptides of the present invention are represented by the following formula:

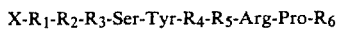

X-$R_1$-$R_2$-$R_3$-Ser-Tyr-$R_4$-$R_5$-Arg-Pro-$R_6$ wherein X is hydrogen or an acyl group having 7 or less carbon atoms; $R_1$ is dehydro Pro or dehydro D-Pro; $R_2$ is D-Phe, Cl-D-Phe, dichloro-D-Phe, $CF_3$-D-Phe, F-D-Phe, difluoro-D-Phe, AcNH-D-Phe, $NO_2$-D-Phe, dinitro-D-Phe, Br-D-Phe, dibromo-D-Phe, $CH_3$-S-D-Phe, $OCH_3$-D-Phe or $CH_3$-D-Phe; $R_3$ is D-Trp or $\beta$-(naphthyl)-D-Ala; $R_4$ is a D-isomer aromatic amino acid or $\beta$-(naphthyl)-D-Ala; $R_5$ is Leu or N$\beta$Me-Leu; and $R_6$ is Gly-$NH_2$ or $NHCH_2CH_3$; provided however that either $R_3$ or $R_4$ is $\beta$-(naphthyl)-D-Ala.

By dehydro Pro is meant 3,4 dehydroproline, $C_5H_7O_2N$, and when X is an acyl radical, it is attached to the nitrogen. By $\beta$-(naphthyl)-D-Ala is meant the D-isomer alanine which is substituted by naphthyl on the $\beta$-carbon atom, which may also be designated 3-(naphthyl)-D-Ala. Preferably $\beta$-(2-naphthyl)-D-Ala is employed; however $\beta$-(1-naphthyl)-D-Ala may also be used.

The peptides of the present invention can be synthesized by classical solution synthesis or by a solid phase technique using a chloromethylated resin, a methylbenzhydrylamine resin (MBHA) or a benzhydrylamine (BHA) resin. The solid phase synthesis is conducted in a manner to stepwise add the amino acids in the chain in the manner set forth in detail in the U.S. Pat. No. 4,211,693. Side-chain protecting groups, as are well known in the art, are preferably added to Ser, Tyr, Arg and His before these amino acids are coupled to the chain being built upon the resin. Such a method provides the fully protected intermediate peptidoresin.

The intermediates of the invention may be represented as:

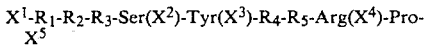

$X^1$-$R_1$-$R_2$-$R_3$-Ser($X^2$)-Tyr($X^3$)-$R_4$-$R_5$-Arg($X^4$)-Pro-$X^5$ wherein: $X^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by $X^1$ are (1) acyl-type protecting groups, such as formyl (For), trifluoroacetyl, phthalyl, p-toluenesulfonyl (Tos), benzoyl (Bz), benzenesulfonyl, o-nitrophenylsulfenyl (Nps), tritylsulfenyl, o-nitrophenoxyacetyl, acrylyl (Acr), chloroacetyl, acetyl (Ac) and γ-chlorobutyryl; (2) aromatic urethan-type protecting groups, e.g., benzyloxycarbonyl (Z) and substituted benzyloxycarbonyl, such as p-chlorobenzyloxycarbonyl, p-nitrobenzyloxycarbonyl, p-bromobenzyloxycarbonyl and p-methoxybenzyloxycarbonyl; (3) aliphatic urethan protecting groups, such as tertbutyloxycarbonyl (Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl (Aly), triphenylmethyl(trityl) and benzyl (Bzl); (7) trialkylsilane groups, such as trimethylsilane. The preferred α-amino protecting group is Boc when X is hydrogen.

$X^2$ is a protecting group for the alcoholic hydroxyl group of Ser and is selected from the group consisting of acetyl, benzoyl, tetrahydropyranyl, tert-butyl, trityl, benzyl and 2,6-dichlorobenzyl. Benzyl is preferred.

$X^3$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl. 2,6-dichlorobenzyl is preferred.

$X^4$ is a protecting group for the nitrogen atoms of Arg and is selected from the group consisting of nitro, Tos, benzyloxycarbonyl, adamantyloxycarbonyl, and Boc; alternatively $X^4$ may be hydrogen, which means there are no protecting groups on the side chain nitrogen atoms of arginine. Tos is preferred.

$X^5$ is selected from the group consisting of Gly-O-$CH_2$-[resin support]; O-$CH_2$-[resin support]; Gly-NH-[resin support]; and OH, ester, amide and hydrazide, of Gly or attached directly to Pro.

The criterion for selecting side chain protecting groups for $X^2$—$X^4$ is that the protecting group must be stable to the reagent under the reaction conditions selected for removing the α-amino protecting group at each step of the synthesis. The protecting group must not be split off under coupling conditions, and the protecting group must be removable upon completion of the synthesis of the desired amino acid sequence under reaction conditions that will not alter the peptide chain.

When the $X^5$ group is Gly-O-$CH_2$-[resin support] or O-$CH_2$-[resin support], the ester moiety of one of the many functional groups of the polystyrene resin support is being represented. When the $X^5$ group is Gly-NH-[resin support], an amide bond connects Gly to BHA resin or to a MBHA resin.

When X is acetyl, formyl, acrylyl, vinylacetyl, benzoyl or some other acyl group having 7 carbon atoms or less, it may be employed as the $X^1$ protecting group for the α-amino group of $R_1$ in which case it can be added before coupling of the last amino acid to the peptide chain. Alternatively, a reaction may be carried out with the peptide on the resin, e.g., reacting with acetic acid in the presence of dicyclohexyl carbodiimide (DCC) or preferably with acetic anhydride.

The fully protected peptide can be cleaved from the chloromethylated resin support by ammonolysis, as is well known in the art, to yield the fully protected amide intermediate. Deprotection of the peptide as well as cleavage of the peptide from the benzhydrylamine resin takes place at 0° C. with hydrofluoric acid (HF). Anisole is added to the peptide prior to treatment with HF. After the removal of HF, under vacuum, the cleaved, deprotected peptide is treated with ether, decanted, taken in dilute acetic acid and lyophilized.

Purification of the peptide is effected by ion exchange chromotography on a CMC column, followed by partition chromatography using the elution system: n-butanol; 0.1 N acetic acid (1:1 volume ratio) on a column packed with Sephadex G-25 or by using HPLC as known in the art.

The peptides of the invention are effective at levels of less than 200 micrograms per kilogram of body weight, when administered at about noon on the day of proestrous, to prevent ovulation in female rats. For prolonged suppression of ovulation, it may be necessary to use dosage levels in the range of from about 0.1 to about 5 milligrams per kilogram of body weight. These antagonists are also effective as contraceptives when administered to male mammals on a regular basis. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

The following examples further illustrate various features of the invention but are intended to in no way limit the scope of the invention which is defined in the appended claims.

EXAMPLE I

The following peptides having the formula X-dehydro Pro-$R_2$-$R_3$-Ser-Tyr-$R_4$-Leu-Arg-Pro-Gly-$NH_2$ are prepared by the solid phase procedure referred to above.

TABLE I

| | X | $R_2$ | $R_3$ | $R_4$ |
|---|---|---|---|---|
| 1 | Ac | 4-F—D-Phe | D-Trp | β-(2-naphthyl)-D-Ala |
| 2 | " | 4-F—D-Phe | β-(2-naphthyl)-D-Ala | D-Trp |
| 3 | " | 3,4-$F_2$—D-Phe | " | " |
| 4 | " | 4-Cl—D-Phe | " | " |
| 5 | " | 4-$NO_2$—D-Phe | " | " |
| 6 | Acr | 4-F—D-Phe | β-(1-naphthyl)-D-Ala | " |
| 7 | " | 4-F—D-Phe | D-Trp | β-(1-naphthyl)-D-Ala |
| 8 | Ac | 4-F—D-Phe | β-(1-naphthyl)-D-Ala | " |
| 9 | " | 4-Cl—D-Phe | β-(2-naphthyl)-D-Ala | " |
| 10 | " | 2,4 $Cl_2$—D-Phe | " | β-(2-naphthyl)-D-Ala |
| 11 | " | 3,4 $Cl_2$—D-Phe | " | " |
| 12 | " | 4-F—D-Phe | " | " |
| 13 | " | 4-$NO_2$—D-Phe | " | " |
| 14 | " | 3,4-$F_2$—D-Phe | " | " |

For purposes of an example, a representative solid phase synthesis of Peptide No. 1 above, which is referred to as [Ac-dehydro Pro$^1$, 4-F-D-Phe$^2$,D-Trp$^3$, β-(2-naphthyl)-D-Ala$^6$]-GnRH is set forth hereinafter. This peptide has the following formula:
Ac-dehydro Pro-4-F-D-Phe-D-Trp-Ser-Tyr-β-(2-naphthyl)-D-Ala-Leu-Arg-Pro-Gly-$NH_2$ A BHA resin is used, and Boc-protected Gly is coupled to the resin over a 2-hour period in $CH_2Cl_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | $CH_2Cl_2$ wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

After step 13, an aliquot is taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. NαBoc protection is used for each of the remaining amino acids throughout the synthesis. NαBoc β-(naphthyl)-D-Ala is prepared by a method known in the art, e.g., as described in detail in U.S. Pat. No. 4,234,571, issued November 18, 1980. The side chain of Arg is protected with Tos. OBzl is used as a side chain protecting group for the hydroxyl group of Ser, and 2-6 dichlorobenzyl is used as the side chain protecting group for the hydroxyl group of Tyr. N-acetyl-dehydro Pro is introduced as the final amino acid. Boc-Arg(Tos) and Boc-D-Trp, which have low solubility in $CH_2Cl_2$, are coupled using DMF $CH_2Cl_2$ mixtures.

The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3 M $NH_4OAc$ in 50/50 methanol/water) followed by partition chromatography in a gel filtration column using the elution system: n-Butanol; 0.1 N Acetic acid (1:1—volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter as $[\alpha]D^{22} = -16.1° \pm 1(c=1, 50\%$ acetic acid).

The peptide assayed in vitro and in vivo. The in vitro test is made using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having a concentration of test peptide ranging from 0.01 to 3 nanomolar. The amount of LH secreted in the samples treated only with GnRH is compared with that secreted by the samples treated with the peptide plus GnRH. Results are calculated to determine the molar concentration ratio of test peptide to GnRH (antagonist/GnRH) required to reduce the amount of LH released by 3 nanomolar GnRH to 50 percent of the control value ($ICR_{50}$) which is found to be 0.005.

The peptide described hereinabove is also used to determine effectiveness to prevent ovulation in female rats. In this test, a specified number of mature female Sprague-Dawley rats, each having a body weight from 225 to 250 grams, is injected with 5 micrograms of peptide in corn oil at about noon on the day of proestrons. Proestrous is the afternoon before estrous (ovulation). A separate female rat group is used as a control to which the peptide is not administered. Each of the control rat females has ovulation at estrous; of the rats treated, none of them ovulated. As a result, the peptide is considered to be significantly effective to prevent ovulation of female rats at a very low dosage, and the peptide is considered to be totally effective at a dose of one milligram.

Peptide No. 2 is similarly synthesized and purified. After amino acid analysis is completed, the optical rotation is measured on a photoelectric polarimeter as $[\alpha]_D^{22} = -69.3° \pm 1(C=1, 50\%$ acetic acid). In vitro testing in similar fashion shows the peptide to have an $ICR_{50}$ of 0.011. In vivo testing at a dosage of 5 μg. shows that 0 out of 10 rats ovulate.

The remaining peptides are similarly tested and are considered to be likewise effective to prevent ovulation of female rats at a very low dosage.

EXAMPLE II

The following peptides having the formula X-dehydro Pro-$R_2$-D-Trp-Ser-Tyr-D-Trp-$R_5$-Arg-Pro-Gly-$NH_2$, as set forth in Table II, are prepared by the solid phase procedure described with respect to Example I.

TABLE II

| PEPTIDE | X | $R_2$ | $R_5$ |
|---|---|---|---|
| 15 | AC | 3,4 $Cl_2$—D-Phe | Leu |
| 16 | " | 4 $CF_3$—D-Phe | " |
| 17 | " | 4 F—D-Phe | " |
| 18 | " | 4 AcNH—D-Phe | " |
| 19 | " | 4 $NO_2$—D-Phe | " |
| 20 | " | 4 Br—D-Phe | " |
| 21 | " | 4 $CH_3$—S-D-Phe | " |
| 22 | " | 4 $OCH_3$—D-Phe | " |
| 23 | " | 4 $CH_3$—D-Phe | " |
| 24 | " | 2,4 $Cl_2$—D-Phe | " |
| 25 | Acr | 3,4 $Cl_2$—D-Phe | " |
| 26 | Ac | 4 $OCH_3$—D-Phe | NχMeLeu |
| 27 | " | 4 $CH_3$—D-Phe | " |
| 28 | " | 3,4 $Cl_2$—D-Phe | " |

Testing is carried out as described with respect to Example I, with the in vivo testing employing dosages of 5 μg. and/or 10 μg. The results are set forth in tabular form in Table IIA.

TABLE IIA

| Peptide | In Vitro $ICR_{50}$ | In Vivo (10 μg) Rats Ovulating | In Vivo (5 μg) Rats Ovulating |
|---|---|---|---|
| 15 | 0.039 | 0/10 | 4/7 |
| 16 | 0.070 | | 7/9 |
| 17 | 0.021 | 0/10 | 0/10 |
| 18 | | 9/10 | |
| 19 | 0.011 | 0/10 | 2/10 |
| 20 | 0.010 | | 5/7 |
| 21 | 0.030 | 1/10 | 7/10 |
| 22 | 0.125 | 3/10 | |
| 23 | 0.044 | 1/7 | 9/9 |
| 24 | | 5/10 | 4/7 |
| 25 | 0.048 | 1/10 | 4/10 |
| 26 | 0.29 | 5/10 | |
| 27 | 0.11 | 3/4 | |
| 28 | 0.05 | 1/3 | 8/10 |

EXAMPLE III

The following peptides having the formula X-$R_1$-pCl-D-Phe-D-Trp-Ser-Tyr-$R_4$-$R_5$-Arg-Pro-$R_6$ are prepared by the solid phase procedure as generally described in Example I except for No. 34 which is prepared on a chloromethylated resin.

TABLE III

| PEPTIDE | X | $R_1$ | $R_4$ | $R_5$ | $R_6$ |
|---|---|---|---|---|---|
| 29 | Ac | dehydro Pro | D-Trp | Leu | Gly-$NH_2$ |
| 30 | " | dehydro Pro | " | NαMeLeu | " |
| 31 | " | dehydro D-Pro | " | Leu | " |
| 32 | " | dehydro D-Pro | " | NαMeLeu | " |
| 33 | Acr | dehydro Pro | " | " | " |
| 34 | Ac | dehydro D-Pro | " | Leu | $NHCH_2CH_3$ |
| 35 | " | dehydro Pro | (imBzl) D-HIS | " | Gly-$NH_2$ |
| 36 | " | dehydro D-Pro | (imBzl) D-HIS | " | " |

The peptides set forth in the foregoing table are assayed in vitro and in vivo as described with respect to Example I. Results are calculated and expressed in Table IIIA 4In Vitro column) as the molar concentration ratio of test peptide to GnRH (antagonist/GnRH) required to reduce the amount of LH released by 3 nanomolar GnRH to 50 percent of the control value (ICR$_{50}$). For the in vivo tests seven, eight, nine or ten mature female Sprague-Dawley rats, each having a body weight from 225 to 250 grams, are injected with 0.02 milligram of peptide (unless otherwise indicated) in corn oil at about noon on the day of proestrous. All of the peptide compositions are considered to be totally effective at a dose of one milligram.

TABLE IIIA

| Peptide | In Vitro ICR$_{50}$ | In Vivo Rats Ovulating |
|---------|---------------------|------------------------|
| 29 | 0.043 | 0/10* |
| 30 | 0.058 | 0/7 |
| 31 | 0.19 | 3/8 |
| 32 | 0.27 | 5/10** |
| 33 | 0.03 | 0/9 |
| 34 | 0.2 | |
| 35 | 0.042 | 4/10 |
| 36 | 0.2 | 10/10 |

*0.025 mg.
**0.010 mg.

These peptides are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, pamoate, malate, ascorbate, tartrate and the like. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

These peptides should be administered under the guidance of a physician, and pharmaceutical compositions will usually contain the peptide in conjunction with a conventional, pharmaceutically-acceptable carrier. Usually, the dosage will be from about 0.1 to about 100 micrograms of the peptide per kilogram of the body weight of the host. Overall, treatment of subjects with these peptides is generally carried out in the same manner as the clinical treatment using other antagonists of GnRH.

These peptides can be administered to mammals intravenously, subcutaneously, intramuscularly, orally, intranasally or intravaginally to achieve fertility inhibition and/or control. Effective dosages will vary with the form of administration and the particular species of mammal being treated. As example of one typical dosage form is a physiological saline solution containing the peptide which solution is administered to provide a dose in the range of about 0.1 to 5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention.

Particular features of the invention are emphasized in the claims that follow.

What is claimed is:

1. A peptide or a nontoxic salt thereof, said peptide having the formula:

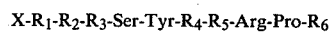

X-R$_1$-R$_2$-R$_3$-Ser-Tyr-R$_4$-R$_5$-Arg-Pro-R$_6$ wherein X is hydrogen or an acyl group having 7 or less carbon atoms; R$_1$ is dehydro Pro or dehydro D-Pro; R$_2$ is D-Phe, Cl-D-Phe, dichloro-D-Phe, CF$_3$-D-Phe, F-D-Phe, difluoro-D-Phe, AcNH-D-Phe, NO$_2$-D-Phe, dinitro-D-Phe, Br-D-Phe, dibromo-D-Phe, CH$_3$-S-D-Phe, OCH$_3$-D-Phe or CH$_3$-D-Phe; R$_3$ is D-Trp or β-(naphthyl)-D-Ala; R$_4$ is selected from the group consisting of β-(naphthyl)-D-Ala, D-Trp, imBzl-D-His, D-Leu and D-Ser(O-tBut); R$_5$ is Leu or N$^\alpha$Me-Leu; and R$_6$ is Gly-NH$_2$ or NHCH$_2$CH$_3$; provided however that either R$_3$ or R$_4$ is β-(naphthyl)-D-Ala.

2. A peptide in accordance with claim 1 wherein R$_2$ is 4-Cl-D-Phe, dichloro-D-Phe, 4-CF$_3$-D-Phe, 4-F-D-Phe, difluoro-D-Phe, 4-AcNH-D-Phe, 4-NO$_2$-D-Phe, dinitro-D-Phe, 4-Br-D-Phe, dibromo-D-Phe, 4-CH$_3$S-D-Phe, 4-OCH$_3$-D-Phe or 4-CH$_3$-D-Phe.

3. A peptide in accordance with claim 2 wherein R$_1$ is dehydro-Pro.

4. A peptide in accordance with either claim 2 or 3 wherein R$_3$ is β-(naphthyl)-D-Ala.

5. A peptide in accordance with claim 4 wherein R$_3$ is β-(2-naphthyl)-D-Ala.

6. A peptide in accordance with either claim 2 or 3 wherein R$_4$ is β-(naphthyl)-D-Ala.

7. A peptide in accordance with claim 6 wherein R$_4$ is β-(2-naphthyl)-D-Ala.

8. A peptide in accordance with claim 4 wherein R$_4$ is β-(naphthyl)-D-Ala.

9. A peptide in accordance with claim 5 wherein R$_4$ is β-(2-naphthyl)-D-Ala.

10. A pharmaceutical composition for regulating the release of gonadotropins comprising as an active ingredient an effective amount of a peptide as defined in claim 1 in association with a major amount of a nontoxic pharmaceutically-acceptable diluent.

11. A peptide which is an antagonist of GnRH and thus inhibits the secretion of gonadotropins by the pituitary gland of mammalians comprising a nonapeptide or decapeptide analog of GnRH having the moiety X-dehydro-Pro at its N-terminal, wherein X is hydrogen or an acyl group having 7 or less carbon atoms, and also having a residue of a D-isomer lipophilic amino acid at the 6-position.

12. A peptide in accordance with claim 11 wherein X is acrylyl.

13. A peptide in accordance with claim 11 wherein X is acetyl.

14. A method for regulating the release of gonadotropins and sex steroids in female and male mammals comprising administering an effective amount of a peptide, or a nontoxic salt thereof, to a mammal, said peptide having the formula:

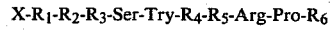

X-R$_1$-R$_2$-R$_3$-Ser-Try-R$_4$-R$_5$-Arg-Pro-R$_6$ wherein X is hydrogen or an acyl group having 7 or less carbon atoms; R$_1$ is dehydro Pro or dehydro D-Pro; R$_2$ is D-Phe, Cl-D-Phe, dichloro-D-Phe, CF$_3$-D-Phe, F-D-Phe, difluoro-D-Phe, AcNH-D-Phe, NO$_2$-D-Phe, dinitro-D-Phe, Br-D-Phe, dibromo-D-Phe, CH$_3$-S-D-Phe, OCH$_3$-D-Phe or CH$_3$-D-Phe; R$_3$ is D-Trp or β-(naphthyl)-D-Ala; R$_4$ is selected from the group consisting of β-(naphthyl)-D-Ala, D-Trp, imBzl-D-His, D-Leu and D-Ser(O-tBut); R$_5$ is Leu or N$^\alpha$Me-Leu; and R$_6$ is Gly-NH$_2$ or NHCH$_2$CH$_3$; provided however that either R$_3$ or R$_4$ is β-(naphthyl)-D-Ala.

15. A method in accordance with claim 14 wherein a female mammal is administered an effective amount to prevent ovulation.

16. A method in accordance with claim 14 wherein a male mammal is administered an effective amount to inhibit spermatogenesis sufficiently to prevent reproduction.

* * * * *